(12) United States Patent
Shimizu et al.

(10) Patent No.: US 9,504,614 B2
(45) Date of Patent: *Nov. 29, 2016

(54) PACKAGED ABSORBENT ARTICLE

(71) Applicant: The Procter & Gamble Company, Cincinnati, OH (US)

(72) Inventors: Yoshiyuki Shimizu, Kobe (JP); Akane Matsuo, Kobe (JP); Sachiko Ninomiya, Kobe (JP); Tsunetoshi Miura, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 15 days.

This patent is subject to a terminal disclaimer.

(21) Appl. No.: 14/547,466

(22) Filed: Nov. 19, 2014

(65) Prior Publication Data

US 2015/0073371 A1 Mar. 12, 2015

Related U.S. Application Data

(63) Continuation of application No. 14/052,836, filed on Oct. 14, 2013, now Pat. No. 8,961,483, which is a continuation of application No. 13/241,596, filed on Sep. 23, 2011, now Pat. No. 8,579,875, which is a continuation of application No. 11/649,499, filed on Jan. 3, 2007, now Pat. No. 8,052,664.

(60) Provisional application No. 60/763,448, filed on Jan. 30, 2006.

(51) Int. Cl.
| | |
|---|---|
| *A61F 13/15* | (2006.01) |
| *A61F 13/551* | (2006.01) |
| *B65D 65/16* | (2006.01) |
| *B65D 85/16* | (2006.01) |
| *A61F 13/47* | (2006.01) |

(Continued)

(52) U.S. Cl.
CPC ....... *A61F 13/5514* (2013.01); *A61F 13/4704* (2013.01); *A61F 13/5611* (2013.01); *B65D 65/16* (2013.01); *B65D 85/16* (2013.01); *A61F 13/551* (2013.01); *A61F 13/5513* (2013.01); *A61F 13/5515* (2013.01); *A61F 13/55135* (2013.01); *A61F 13/84* (2013.01); *A61F 2013/8497* (2013.01)

(58) Field of Classification Search
CPC .................... A61F 13/55135; A61F 13/5513; A61F 13/5515; A61F 2013/55155
USPC ............ 604/385.02, 385.01, 385.05, 385.03; 206/438
See application file for complete search history.

(56) References Cited

U.S. PATENT DOCUMENTS

| | | | | |
|---|---|---|---|---|
| 3,193,181 A | * | 7/1965 | Konjevich | ............. B65D 75/28 206/496 |
| 3,244,318 A | | 4/1966 | Berryman et al. | |

(Continued)

FOREIGN PATENT DOCUMENTS

| | | |
|---|---|---|
| JP | 03021237 A | 1/1991 |
| JP | 8-500502 | 1/1996 |

(Continued)

OTHER PUBLICATIONS

PCT International Search Report dated May 18, 2007, 61 pages.

*Primary Examiner* — Jacqueline Stephens
(74) *Attorney, Agent, or Firm* — Andrew J. Hagerty

(57) ABSTRACT

A packaged absorbent article having a body surface and a garment surface; and a wrapper sheet for wrapping the absorbent article so that at least a portion of the garment surface of the absorbent article can be seen through the wrapper sheet.

4 Claims, 1 Drawing Sheet

(51) Int. Cl.
  *A61F 13/56* (2006.01)
  *A61F 13/84* (2006.01)

(56) References Cited

U.S. PATENT DOCUMENTS

| | | | |
|---|---|---|---|
| 5,702,376 A * | 12/1997 | Glaug et al. | 604/361 |
| 6,632,974 B1 | 10/2003 | Suzuki et al. | |
| 8,052,664 B2 | 11/2011 | Shimizu et al. | |
| 8,220,632 B2 | 7/2012 | Oi et al. | |
| 8,579,875 B2 | 11/2013 | Shimizu et al. | |
| 2003/0109839 A1 | 6/2003 | Costea et al. | |
| 2003/0114809 A1 | 6/2003 | Gagliardi et al. | |
| 2003/0120241 A1 * | 6/2003 | Sorebo | A61F 13/551 604/385.02 |
| 2004/0015145 A1 | 1/2004 | Miura et al. | |
| 2004/0149613 A1 * | 8/2004 | Mizutani | A61F 13/47209 206/440 |
| 2004/0186450 A1 * | 9/2004 | Hermansson | B65D 75/58 604/385.01 |
| 2004/0238393 A1 | 12/2004 | Ohi et al. | |
| 2005/0019514 A1 | 1/2005 | Takegawa et al. | |
| 2005/0029143 A1 | 2/2005 | Samolinski et al. | |
| 2005/0145523 A1 | 7/2005 | Zander et al. | |
| 2005/0154365 A1 | 7/2005 | Zander et al. | |
| 2006/0144736 A1 * | 7/2006 | Goodrich | A61F 13/15203 206/440 |
| 2007/0293834 A1 | 12/2007 | Miura et al. | |
| 2014/0039439 A1 | 2/2014 | Shimizu et al. | |

FOREIGN PATENT DOCUMENTS

| | | |
|---|---|---|
| JP | 09087405 A | 3/1997 |
| JP | 2000238875 A | 9/2000 |
| JP | 2003199786 A | 7/2003 |
| JP | 2005103065 A | 4/2005 |
| JP | 2005185858 A | 7/2005 |
| WO | WO 02/094151 A1 | 11/2002 |

* cited by examiner

PACKAGED ABSORBENT ARTICLE

FIELD OF THE INVENTION

The present invention relates to absorbent articles. More particularly, the present invention relates to absorbent articles wrapped by a wrapper sheet.

BACKGROUND OF THE INVENTION

Absorbent articles such as sanitary napkins, pantiliners and incontinent pads are devices that are typically worn in the crotch region of an undergarment. More specifically, sanitary napkins and pantiliners, for example, are worn by women in a pair of panties that is normally positioned between the wearer's legs, adjacent to the perineum area. Sanitary napkins and pantiliners are designed to absorb and retain body fluids or discharges (e.g., urine and menses) from the body of women and to prevent body and clothing from soiling. A wide variety of shapes and dimensions of sanitary napkins and pantiliners is currently used by women for the collection of body fluids.

Recent developments for disposable absorbent articles tend to focus on not only improvement of their product functions (e.g., superior absorbency, leakage protection and comfort) but their aesthetic features. This trend is particularly true for sanitary napkins and baby diapers. Such disposable absorbent articles are disclosed in, for example, WO 2004/006818 published on Jan. 24, 2004.

The aesthetic designs are typically implemented by printing or otherwise providing graphics on one (or more) of component members of those disposable absorbent articles (e.g., a backsheet). It is believed that such aesthetic features can provide emotional benefit to users, and thus, for example, in the case of sanitary napkins, may decrease users' melancholic mood during the menstruation period. In diaper embodiments, the graphics may provide the diaper wearer or caregiver with a pleasant or interesting design.

Some disposable absorbent articles (typically sanitary napkins and pantiliners) are folded and wrapped individually by a wrapper sheet. The materials of such wrapper members are typically polyethylene films or sometimes nonwoven materials which are not necessarily transparent. In some cases, this is intentional because consumers of such disposable absorbent articles do not want other people to notice or show they are carrying the articles, such as sanitary napkins. Also, in some cases, the wrapper sheet is used for disposal of the used product and, as such, a non-transparent wrapper can prevent the soiled article from being seen through the wrapper sheet. These needs, however, are generally contrary to desirability of showing the aesthetic features of disposable absorbent articles through the wrapper sheet.

Thus, it may be desirable to provide an individually packaged absorbent article that can show an aesthetic feature of the absorbent article through a wrapper sheet while controlling the visibility of a soiled absorbent article disposed in the wrapper sheet after use.

SUMMARY OF THE INVENTION

In order to meet the desired attributes noted above, the present invention provides an individually packaged absorbent article including an absorbent article having a body surface and a garment surface; and a wrapper sheet for wrapping the absorbent article so that at least a portion of the garment surface of the absorbent article can be seen through the wrapper sheet. The wrapper sheet has an opacity of about 8.5 to about 50, a total color difference of about 10 to about 75, and a UV transmittance of about 0 to about 3.5.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

Figure 1:
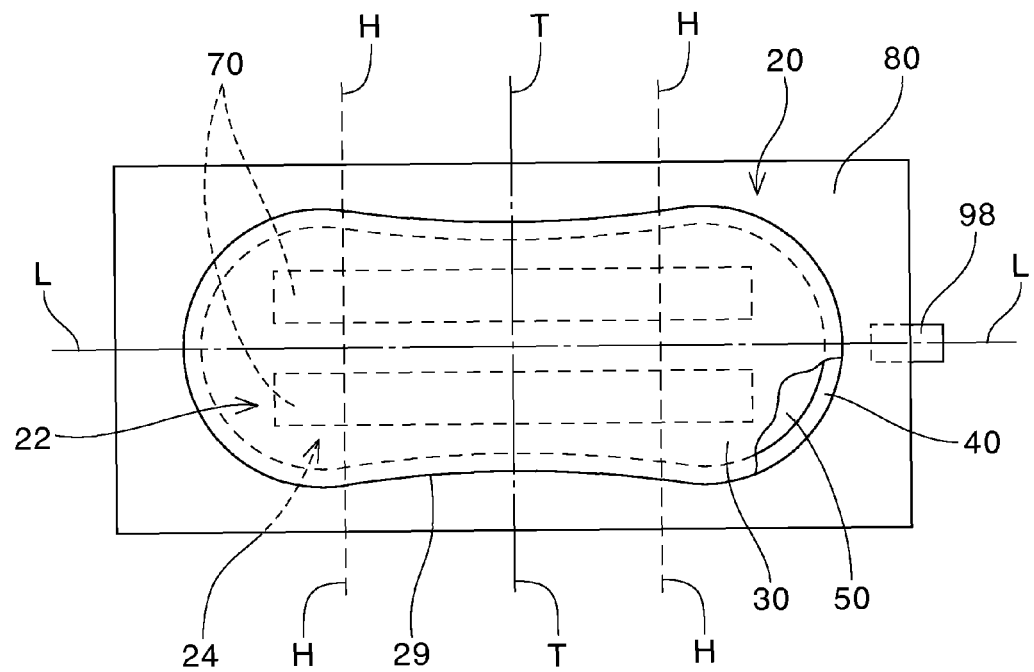
FIG. 1 is a top plan view of an absorbent article (i.e., a sanitary napkin) embodiment of the present invention.

Herein, "absorbent article" refers to articles which absorb and/or contain body exudates or discharges such as body fluids, and is intended to include sanitary napkins, pantiliners, diapers, and incontinence pads and other absorbent articles intended to be worn by a wearer).

Herein, "disposable" refers to articles which are intended to be discarded after a single use, composted, or otherwise disposed of in an environmentally compatible manner. (That is, they are not intended to be laundered or otherwise restored or reused as an absorbent article.)

Herein, "sanitary napkin" refers to articles which are worn by females adjacent to the pudendal region which are intended to absorb and contain the various exudates which are discharged from the body (e.g., blood, menses, and urine).

Herein, "body surface" refers to surfaces of absorbent articles and/or their component members which face the body of the wearer, while the term "garment surface" refers to the opposite surfaces of the absorbent articles and/or their component members that face away from the wearer when the absorbent articles are worn. Absorbent articles and components thereof, including the topsheet, backsheet, absorbent core, and any individual layers of their components, have a body surface and a garment surface.

Herein, "color system" refers to groups of colors which are different but similar one another. Color systems include a blue color system, a pink color system, a orange color system, an yellow color system, and an green color system. Color systems can be defined by the International Commission on Illumination (CIE), i.e., CIE L*a*b hue angle. For example, "blue color system" is defined as CIE L*a*b hue angle ranging from −40 degrees to −145 degrees, "pink color system" is defined as CIE L*a*b hue angle ranging from −40 degrees to 20 degrees, "orange color system" is defined as CIE L*a*b hue angle ranging from 20 degrees to 55 degrees, "yellow color system" is defined as CIE L*a*b hue angle ranging from 55 degrees to 110 degrees, and "green color system" is defined as CIE L*a*b hue angle ranging from 110 degrees to −145 degrees.

Herein, "graphic" refers to a pattern that is constituted by a shape(s), a figure(s), a symbol(s) or character(s), a color difference or transition of at least two colors, and the like. The graphic may have an aesthetic image, design and/or color that can provide emotional benefit(s) when the absorbent article having the graphic is looked or viewed by users. The graphic may include other element(s) than the aesthetic image, design and/or color, for example, information such as the usage information and/or the size of the absorbent article, an indication of the front/back of the absorbent article, a brand name or logo of the absorbent article, and the like. In certain embodiments, the colors of the graphic are selected from one of the above described color systems, e.g. the blue color system. However, if desired, the colors of the graphic can be selected from two or more color systems, e.g., the blue color system and the pink color system. The graphic is typically formed by a printing process known in the art, but is not limited to printing.

Herein, "coloration treatment" refers to a treatment for making a color change in a material from its original color. In most cases, since component materials of the absorbent article typically have a white color, the coloration treatment changes the original white color to a non-white color (e.g., blue, red, yellow, green, gray, etc). Such a color change can be implemented by any technology known in the art. In one typical example, the coloration treatment is implemented by introducing or mixing a non-white color pigment(s) into the ingredient material(s) of an original material. In another typical example, the coloration treatment is implemented by printing on an original material. Coloration treatment by printing can be implemented by any conventional printing method or technology known in the art, including, but not limited to, a gravure printing, a flexography printing, a letter press printing, an offset printing, an ink jet printing, and the like.

In certain embodiments, a coloration treatment may provide one non-white color which occupies in total the greatest area of a specified material compared with the other non-white color(s), if any. Such a "non-white color" is hereinafter referred to as "primary color". For example, when a particular film has a coloration treatment, it means the polyethylene film may have one non-white color as the primary color which occupies the greatest area of the film compared with the other non-white color(s) if any within the film.

FIG. 1 is a top plan view of one exemplary disposable absorbent article, sanitary napkin 20, of the present invention. The sanitary napkin 20 (and its component members) has a body surface 22, and a garment surface 24 opposed to the body surface 22. The sanitary napkin 20 shown in FIG. 1 is viewed from the body surface 22. The sanitary napkin 20 has a circumferential edge 29 which defines the outermost edge of the sanitary napkin 20.

The sanitary napkin 20 has two centerlines, a longitudinal centerline L and a transverse centerline T. Herein, "longitudinal" refers to a line, axis or direction in the plane of the sanitary napkin 20 that is generally aligned with (e.g., approximately parallel to) a vertical plane which bisects a standing wearer into left and right body halves when the sanitary napkin 20 is worn. Herein, "transverse" or "lateral", are interchangeable, and refer to a line, axis or direction which lies within the plane of the sanitary napkin 20 that is generally perpendicular to the longitudinal direction.

The sanitary napkin 20 includes three primary components. These include a liquid permeable topsheet 30, a liquid impermeable backsheet 40, and an absorbent core 50 disposed between the topsheet 30 and the backsheet 40. The top surface of the topsheet 30 forms the body surface 22 of the sanitary napkin 20, while the bottom surface of the backsheet 40 forms the garment surface 24 of the sanitary napkin 20. The sanitary napkin 20 further includes a wrapper sheet 80 which is disposed adjacent to at least a portion of the garment surface 24 of the sanitary napkin 20. The wrapper sheet 80 shown in FIG. 1 further includes a reseal tape 98 which is disposed at one end edge of the wrapper sheet 80 generally along the longitudinal center line L. The sanitary napkin 20 shown in FIG. 1 may be folded along two folding lines H together with the wrapper sheet 80 to produce an individually packaged configuration.

Figure 2:
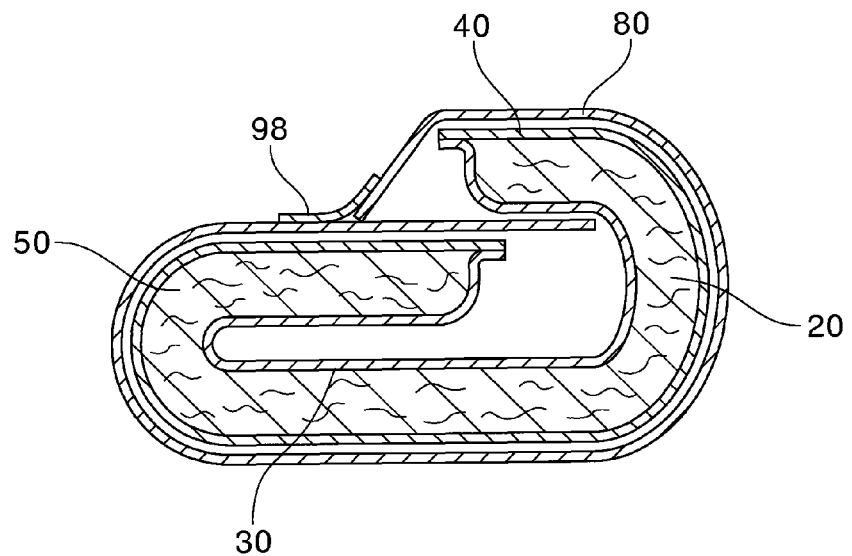
FIG. 2 is a cross-sectional view of the sanitary napkin shown in FIG. 1, taken along the longitudinal center line, in a folded configuration.

FIG. 2 is a cross-sectional view of the sanitary napkin 20 shown in FIG. 1 (taken along the longitudinal center line L), which shows the sanitary napkin 20 such an individually packaged configuration. In this embodiment, the sanitary napkin 20 is folded together with the wrapper sheet 80 along the two folding lines H shown in FIG. 1. After being folded, one end of the wrapper sheet 80 is joined to a portion of the outer surface of the wrapper sheet 80 by means of the reseal tape 98, thereby forming the individual package shown in FIG. 2. After a soiled sanitary napkin is wrapped by the wrapper sheet 80, the reseal tape 98 can be also used for closing (or "resealing") the wrapper sheet 80 for forming a disposal configuration.

The number of the folding lines can be changed depending on the size or the design of the sanitary napkin 20. For example, the number of the folding lines can be one, three, or more if desired.

In certain embodiments, the sanitary napkin 20 may have no folding line, i.e., it is not folded, and the unfolded sanitary napkin is simply put into a pouch which is formed by a sheet material (hereinafter, such a sheet material is also referred to as "wrapper sheet"). In certain embodiments, a folded sanitary napkin (i.e., folded by itself or not folded together with the wrapper sheet) can be put into a pouch formed by a wrapper sheet.

In certain embodiments, the wrapper sheet may have an opacity of about 8.5% to about 50%, a total color difference of about 10 to about 75, and a UV transmittance of about 0 to about 3.5. The wrapper sheet may have an opacity of about 15% to about 45% or about 15% to about 40%, a total color difference of about 30 to about 70 or about 30 to about 65, and/or a UV transmittance of about 0 to about 3 or about 0 to about 2.

In certain embodiments, the wrapper sheet may have an opacity of about 8.5 to about 50, a total color difference of about 10 to about 90, a speculum gloss of about 0.1 to about 5.5, and a UV transmittance of about 0 to about 3.5. The wrapper sheet has an opacity of about 15% to about 45% or about 15% to about 40%, a total color difference of about 20 to about 80 or about 25 to about 75, a speculum gloss of about 0.1 to about 5 or about 1 to about 4.5, and/or a UV transmittance of about 0 to about 3 or about 0 to about 2.

The garment surface of the absorbent article has a first coloration treatment, while the wrapper sheet has a second coloration treatment. The wrapper sheet may have an opacity of 8.5-50, a total color difference of 30-75, and/or a hue angle difference of about 0 to about 90 which is defined between the first and second coloration treatments. The wrapper sheet may have an opacity of about 15% to about 45% or about 15% to about 40%, a total color difference of about 30 to about 70 or about 30 to about 65, and/or a hue angle difference of about 0 to about 60 or about 0 to about 25.

The wrapper sheet may have an opacity of about 8.5 to about 50, a total color difference of about 10 to about 75, a UV transmittance of about 0 to about 3.5, and/or a hue angle difference of about 0 to about 90 which is defined between the first and second coloration treatments. The wrapper sheet may have an opacity of about 15% to about 45% or about 15% to about 40%, a total color difference of about 30 to about 70 or about 30 to about 65, a UV transmittance of about 0 to about 3 or about 0 to about 2, and/or a hue angle difference of about 0 to about 60 or about 0 to about 25.

The first and second coloration treatments may produce first and second primary colors which are selected from one color system. More specifically, in certain embodiments, the garment surface of the absorbent article and the wrapper sheet may have first and second coloration treatments producing first and second primary colors, respectively, which are selected from a color system which is selected from the group consisting of a blue color system, a pink color system, a green color system, an orange color system, and a yellow color system.

The wrapper sheet may have an opacity of about 8.5% to about 50%, a speculum gloss of about 0.1 to about 5.5, and/or a UV transmittance of about 0 to about 3.5. The wrapper sheet has an opacity of about 15% to about 45% or about 15% to about 38%, a speculum gloss of about 0.1 to about 5 or about 1 to about 4.5, and/or a UV transmittance of about 0 to about 3 or about 0 to about 2).

The optical properties of the wrapper sheet and/or the other component material(s) of the absorbent articles, i.e., the opacity (OP), the total color difference ($\Delta^*E$), the hue angle difference ($\Delta h$), the speculum gloss (Gs), and/or the UV transmittance (UVT), controlled by, for example, changing the kinds and amount of ingredients, the printing manner, or the physical surface treatment of the wrapper sheet material or the component material(s) of the absorbent articles.

The opacity of a sheet material shows the degree of un-clearness or un-transparency of the sheet material. When a sheet material has an opacity of 0%, the sheet material is completely transparent. On the other hand, if a sheet material has an opacity of 100%, the sheet material has no transparency, i.e., no light is transmitted through the material. The opacity of the wrapper sheet shows the degree on how clearly the absorbent article individually packaged by the wrapper sheet can be seen through the wrapper sheet. In general, when the opacity of the wrapper sheet material is within certain lower ranges (e.g., about 8.5% to about 50%), it may help the user to see feature(s) of the absorbent article through the wrapper sheet. Such features may include, for example, the type (e.g., a wing type of sanitary napkin or not), the graphic, the color of the absorbent article, and the like. Thus, when the absorbent article has such a feature, the feature may be recognized through the wrapper sheet. For example, when the absorbent article has an atheistic feature such as a printed graphic feature on the garment surface, the feature may be seen through the wrapper sheet. Accordingly, in such embodiments, the individually packaged absorbent article can provide the graphic benefit without printing the graphic on the wrapper sheet. This may provide an opportunity to decrease the material cost for the wrapper sheet since it can eliminate the need of printing graphics on the wrapper sheet. In another example, if the absorbent article is a sanitary napkin which has a pair of flaps (or wings), the flap feature also can be seen through the wrapper sheet. Thus, the user who carries the sanitary napkin in her bag does not need to remember what type of sanitary napkin she has in the bag.

The total color difference of a sheet material shows the degree of the color difference (or distance) of the primary color of the sheet material from the standard white color ($L^*=93.95$, $a^*=0.26$, $b^*=4.95$). The total color difference of the wrapper sheet shows the degree of the color strength of the wrapper sheet compared to the standard white color. In general, when the total color difference of the wrapper sheet material is within a certain range (e.g., about 10 to about 75), the visibility of the soiled absorbent article seen through the wrapper sheet after use can be controlled. This is beneficial since it can help prevent the color of the body fluids absorbed by the soiled napkin from being directly seen or recognized through the wrapper sheet, after the soiled sanitary napkin is wrapped by the wrapper sheet for disposal. It may also provide some emotional benefit(s) which is caused by the color of the wrapper sheet when the absorbent article of the invention is looked or viewed by the user. Such emotional benefits include, but not limited to, a relaxed or comfortable feeling (or impression), a happy or pleasant feeling, an encouraged feeling, and the like. In particular, when a color(s) is a key element of the product image or concept (i.e., "brand equity element"), the total color difference of the wrapper sheet can contribute to the transfer of the image to the user of the absorbent article.

The speculum gloss of a sheet material can affect the impression of the sheet material, in particular the impression of appearance, texture/touch, tactile of the sheet material. In general, when the speculum gloss of the wrapper sheet is within certain lower range (e.g., about 0.1 to about 5.5), it can also provide some emotional benefit(s) such as soft image of the product (e.g., soft appearance image, soft texture/touch image, and soft tactile image) as well as high quality image of the product. Thus, an absorbent article having such a wrapper sheet may be preferred by consumers.

The UV transmittance of a sheet material shows the ratio of UV light which can penetrate the sheet material. When a sheet material has a UV transmittance of 100%, all power of the UV light penetrates the sheet material and reaches the absorbent article, and thus may affect the quality of the component materials (e.g., adhesive) of the absorbent article. On the other hand, if a sheet material has a UV transmittance of 0%, no UV light penetrates the sheet material, and thus the quality of the component materials of the absorbent article may be protected. So, when the UV transmittance of the wrapper sheet material is within a certain lower range (e.g., about 0% to about 3.5%), it can prevent the quality of the component material(s) from being affected by the UV light. In particular, it can prevent the adhesive material(s) used in the absorbent article from being damaged by the UV light. Also, it can prevent the color(s) of the printed material(s) used in the absorbent article from being changed by the UV light.

The hue angle difference shows the degree of the hue difference (or distance) between two colors. The hue angle difference of a wrapper sheet is the degree of the hue difference (or distance) between the primary color of the first color treatment of the garment surface of the absorbent article (e.g., the backsheet or the removable release sheet) and the primary color of the second color treatment of the wrapper sheet. In general, when the hue angle difference of a wrapper sheet is within a certain range (e.g., about 0 to about 90), it may provide some emotional benefit(s) caused by the combination of the colors between the wrapper sheet and the garment surface of the absorbent article. Such emotional benefits include, but not limited to, a relaxed, comfortable, or stable feeling (or impression), a happy or pleasant feeling, an encouraged feeling, and the like. On the other hand, if the hue angle difference of a wrapper sheet is beyond that range, it may cause some emotional unbalance such as a unstable feeling (impression), an uncomfortable feeling, and the like. So, it may be desirable that the hue angle difference of a wrapper sheet is within certain range to provide positive emotional benefit(s).

The wrapper sheet may be manufactured from a thin flexible material. The wrapper sheet material may be liquid impermeable. The wrapper sheet may be in the form of a film or a nonwoven web.

Materials suitable for the wrapper sheet of the present invention typically include a thermoplastic polymer, a pigment and a filler (inorganic or organic). The materials for the pigment and filler may be in the form of a particle. Such particles may be dispersed in the thermoplastic polymer. Generally, pigments or fillers are contained in no more than about 20% of a film. (If desired, the particles of the pigment or the filler can be coated with a fatty acid ester to obtain higher loadings in the polymer.)

In certain embodiments, the optical properties of the wrapper sheet, i.e., the opacity (OP), the total color difference ($\Delta^*E$), the hue angle difference ($\Delta h$), the speculum gloss (Gs), and the UV transmittance (UVT), may be controlled by changing the kinds and amount of ingredients, the printing manner, or the physical surface treatment of the wrapper sheet material.

Examples of suitable thermoplastic polymers include polyolefin such as polyethylene (PE), including a liner low density polyethylene (LLDPE), a low density polyethylene (LDPE), a ultra low density polyethylene (ULDPE), a high density polyethylene (HDPE), a polypropylene, and a mixture thereof. Other suitable thermoplastic polymers which may also be used include, but are not limited to, a polyester, a polyurethane, a compostable or biodegradable polymer, a thermoplastic elastomer, and a metallocene catalyst-based polymer.

The material for the filler may be an inorganic material which is selected from the group consisting of a titanium dioxide, a zinc oxide, a calcium carbonate, a mica and a mixture thereof. Alternatively (or if desired), the material for the filler can be an organic material such as a high-density polyethylene or other organic polymer material such as a polypropylene.

In a manufacture process, the thermoplastic polymer, filler and pigment may be mixed or blended together to form a homogeneous mixture in a suitable mixing extrude, or in a separate preliminary compounding step. The mixture may then be cast or blown into a film or a nonwoven web.

The optical properties of the wrapper sheet can be controlled by changing the kinds and amount of ingredients of the ink(s) to be used for printing the surface of the wrapper sheet material. Such printing can be done by any conventional printing methods know in the art including gravure printing, flexography printing, letter press printing, offset printing, ink jet printing, and the like. Typically, a printing ink contains about 60% of a binder resin, about 40% of a pigment (or dye), and an amount of additives, such as process aid(s), which are typically used for drying up the solvents after the printing process.

The amount of the filler can affect the opacity level of the wrapper sheet. For example, increasing the filler material can make the resultant material more translucent, while decreasing the filler material can make the resultant material more transparent. Thus, in certain embodiments, the opacity level of the wrapper sheet 80 may be controlled by changing the amount fillers contained in the wrapper sheet material.

The opacity level of the wrapper sheet can also be controlled by the kinds and amount of ingredients of the ink(s) to be used for printing the surface of the wrapper sheet material. In order to increase the opacity level, an ink which contains an inorganic pigment(s) such as a titanium dioxide, a zinc oxide, a calcium carbonate, and the like may be used. Such inorganic pigment(s) can provide higher opacity by increasing its amount. The particle size of the inorganic pigment(s) can vary depending on the printing method to be employed. In certain embodiments, a titanium dioxide may be used as the pigment.

In certain embodiments, the wrapper sheet has a coloration treatment which produces a primary color by tinting, i.e., adding a pigment(s) into the film ingredients. The pigment(s) may be selected depending on the target coloration treatment. An appropriate selection of a pigment(s) contributes to a production of a wrapper sheet having an expected non-white color (e.g., blue, red, yellow, green, gray, etc). The wrapper sheet having a coloration treatment can also be produced by changing the kinds and amount of ingredients of the ink(s) to be used for printing the surface of the wrapper sheet material.

In certain embodiments, the speculum gloss level of the wrapper sheet may be controlled by a micro emboss treatment (or a mat treatment) formed at one surface of the wrapper sheet. Herein "micro emboss treatment" is a physical surface treatment at a surface of a film material that produces a change of the speculum gloss level at the surface of the film material. Typically, after the formation of a wrapper sheet material, such a micro emboss treatment is implemented to produce a wrapper sheet having a mat texture. Such a micro emboss treatment can be implemented during a casting process by nipping at a casting machine at a casting process. Additionally or alternatively, such a micro emboss treatment can be implemented by embossing after re-heating the wrapper sheet material in a blowing process.

The speculum gloss level of the wrapper sheet can controlled by introducing an inorganic or organic contaminant(s) in the printing ink(s) or layer(s). The average particle size of such contaminant(s) are selected such that it can make the printed surface mat and rough enough to provide the same or similar effect given by the micro emboss treatment. The average particle size of such contaminant(s) can vary depending on the printing method to be employed. In a certain embodiments, particles of a titanium dioxide may be used.

Examples of suitable wrapper sheet materials are shown in Table 1 below. (Some suitable combinations of the wrapper sheet material and the release paper are: (1) the Sample No. 1 or 2 and Sample No. 6; and (2) the Sample No. 3 or 4 and Sample No. 7.)

TABLE I

| Sample No. | Material | Code No. | Supplier | Basis Weight (g/m$^2$) |
|---|---|---|---|---|
| 1 | PE film | PG-ST952-GR-M9635 | Steller Flims Sdn Bhd | 24.0 |
| 2 | PE film | PG-ST952-GR-M9642 | Steller Flims Sdn Bhd | 24.0 |
| 3 | PE film | PG-ST952-LB-M8825 | Steller Flims Sdn Bhd | 24.0 |
| 4 | PE film | PG-ST952-LB-M8826 | Steller Flims Sdn Bhd | 24.0 |
| 5 | PE film | PG-ST952-WH | Steller Flims Sdn Bhd | 24.0 |
| 6 | Silicone Paper | BL35G MGA Silox D3H/0 PG 1182 | Akrosil Release Products | 37.0 |
| 7 | Silicone Paper | BL35G MGA Silox D3H/0 PG 1020 | Akrosil Release Products | 37.0 |

| Sample No. | OP (%) | $\Delta^*E$ | $\Delta h$ | Gs | UVT (%) |
|---|---|---|---|---|---|
| 1 | 38.3 | 31.5 | 129.5 | 3.6 | 0.83 |
| 2 | 31.2 | 48.6 | 135.4 | 4.0 | 1.12 |
| 3 | 23.6 | 33.3 | −129.3 | 4.0 | 1.61 |
| 4 | 26.0 | 59.4 | −120.9 | 4.0 | 1.25 |
| 5 | 18.6 | 6.4 | 101.5 | 3.7 | 3.10 |
| 6 | NA | 37.8 | 124.1 | NA | NA |
| 7 | NA | 30.6 | −138.6 | NA | NA |

(OP: Opacity (%); $\Delta^*E$: Total Color Difference; $\Delta h$: Hue Angle Difference; Gs: Speculum Gloss; UVT: UV transmittance (%))

The topsheet 30 is generally compliant, soft feeling, and non-irritating to the wearer's skin. Further, the topsheet 30 is at least partially liquid permeable or pervious, permitting body fluids (e.g., menses and/or urine) to penetrate through its thickness. One example of a material suitable for the topsheet 30 is a macroscopically expanded, three-dimensional formed polyethylene film, such as, for example, the macroscopically expanded, three-dimensional formed polyethylene film available from Tredegar Film Products, Indiana, USA, under Code No. X-27121.

The backsheet 40 may be impervious to body fluids and is generally manufactured from a thin plastic film, although other flexible liquid impervious materials may also be used. The backsheet 40 generally prevents the body fluids absorbed and contained in the absorbent core 50 from wetting articles which contact the absorbent article such as bedsheets, pants, pajamas and undergarments. The backsheet 40 may thus include a woven or nonwoven material, polymeric films such as thermoplastic films of polyethylene or polypropylene, or composite materials such as a film-coated nonwoven material. The backsheet 40 can be embossed to provide a more clothlike appearance.

The backsheet 40 can include a single layer material, or two or more layers of materials. One suitable backsheet material is a single layer polyethylene film which is available from Daedong Co. Ltd., KyungBuk-Do, Korea, under Code No. DNF-0417C.

The backsheet 40 may have a graphic(s) printed thereon. In one embodiment, the colors of the graphic are selected from one color system. However, if desired, they can be selected from more than one color system.

The backsheet 40 may have a coloration treatment which produces a primary color. Such a primary color is selected from the group consisting of a blue color system, a pink color system, a green color system, an orange color system, and a yellow color system.

The absorbent core 50 is generally capable of receiving, absorbing or retaining body fluids discharged. The absorbent core 50 may be compressible, conformable, and non-irritating to the wearer's skin. The absorbent core 50 can be formed by a single layer material or a plurality layers of materials. The absorbent core may include any of a wide variety of liquid-absorbent materials commonly used in absorbent articles, such as comminuted wood pulp, which is generally referred to as airfelt. In certain embodiments, the absorbent core may include an air laid tissue material.

The garment surface 24 of the sanitary napkin 20 (or the backsheet 40) may include fastening means for attaching the sanitary napkin 20 to the wearer's undergarment. Such fastening means may include a panty fastening adhesive 70. The panty fastening adhesive 70 is adapted to secure the sanitary napkin 20 to the crotch region of an undergarment. Any types of fasteners known in the art, such as adhesive fasteners and mechanical fasteners can be used. One example of a suitable panty fastening adhesive 70 is a pressure-sensitive adhesive. In the embodiment shown in FIG. 1, the panty fastening adhesive 70 includes a pair of spaced apart longitudinally-oriented strips of adhesive that are centered about the longitudinal centerline L.

The panty fastening adhesive 70 may be protected by a fastener protection means before use. Such a fastener protection means may be releasably attached to the panty fastening adhesive 70. The fastener protection means keeps the quality of the panty fastening adhesive 70 and prevents it from sticking to other portions of the sanitary napkin 20 unintentionally prior to use. The fastener protection means may be a removable release sheet which is a separate member from the wrapper sheet 80.

The removable release sheet can be formed by any sheet materials known in the art, such as a paper material or a film material. One exemplary suitable material for the removable release sheet is a silicone coated paper which has at least one surface coated with a release coating material. Such a release coating can be made from any material known in the art. The release sheet may be attached to the inside surface of the wrapper sheet 80 at a few portions by means of an adhesive.

In certain embodiments, the removable release sheet is transparent or translucent such that the garment surface 24 of the backsheet 40 can be seen through the release sheet.

It should be noted that the outer surface (or the opposite surface to the release coating surface) of the removable release sheet forms at least a part of the garment surface 24 of the sanitary napkin 20. Therefore, the garment surface 24 of the sanitary napkin 20 can include not only the bottom surface of the backsheet 40 but the outer surface of the removable release sheet.

In certain embodiments, the removable release sheet may have one or more graphics printed on it. The colors of the graphic may be selected from one color system. However, if desired, they can be selected from more than one color system.

The removable release sheet may have a coloration treatment which produces a primary color. Such a primary color may be selected from the group consisting of a blue color system, a pink color system, a green color system, an orange color system, and a yellow color system.

In certain embodiments, the fastener protection means may be a release coating formed on the inside surface (i.e., the napkin facing surface) of the wrapper sheet 80. Such a coating can comprise any material known in the art, with silicone coatings being examples of suitable coatings. The coating 82 may be provided by coating only that zone of the wrapper sheet 80 which will substantially contact the panty fastening adhesive 70. Alternatively, the entire inside surface of the wrapper sheet 80 may be coated. An exemplary structure of coating the entire inside of a wrapper is disclosed in U.S. Pat. No. 5,181,610 entitled "Flexible Container with Nonstick Interior" issued to Quick et al. on Jan. 26, 1993.

As shown in FIG. 2, the sanitary napkin 20 of the invention may be wrapped by the wrapper sheet 80. In certain embodiments, a folded (or un-folded if desired) sanitary napkin may be put in a pouch, as conventionally well known in the art. Such a pouch may be formed by folding and sealing the edges of a wrapper sheet.

As shown in FIGS. 1 and 2, the wrapper sheet 80 and the sanitary napkin 20 may be folded together around two fold lines H (however, the number of fold lines can be zero or any other number) to provide an individually packaged structure for the sanitary napkin 20.

The sanitary napkin 20 may include one or more flaps or wings as are known in the art. A preferred flap structure for sanitary napkins is disclosed in U.S. Pat. No. 6,074,376 issued to Mills on Jun. 13, 2000.

The sanitary napkins can be individually wrapped by a wrapper sheet or wrapped in any number. Further, the individually or otherwise wrapped articles can be contained in a package such as a bag of polymeric film, or a box.

Test Methods

This section describes methods for determining an opacity, a total color difference, a speculum gloss, and a UV transmittance of a sheet material, and a hue angle difference which is defined between two sheet materials having first and second coloration treatments, respectively.

I. Opacity (OP)

A dispersion colorimeter is preferably used for determining the opacity of a sample material. A preferred dispersion colorimeter is available from BYK-Gardner GmbH, Geretsried, Germany, under Trade Name "BYK Gardner Color-Guide 45/0" (Cat. No. 6800).

The measurements should be conducted by using a light source "A" at a viewing angle of 2° (degrees).

This dispersion colorimeter includes a light source for Illuminant A (i.e., an approximation of incandescent lamp having a correlated color temperature of about 3000 K), a flat table, a white standard plate, a standard black plate, a photo detector which includes a multi-celled photo-detector diode array, and a computer. The white and black standard plates are available from the same company under Cat. Nos. 6811 and 6810, respectively.

In the measurement, the white standard plate is placed on the flat table. A sample material is put on the white standard plate in a flat state. The sample material is illuminated by the light source with an incident angle of 45°. The reflection light which is reflected from the sample material is received by the photo detector with a receiving angle of 0°. The reflection rate (Yw) of the reflection light is detected by the photo detector. Similarly, after the black standard plate is placed on the flat table, the sample material is put on the black standard plate in a flat state. The sample material is illuminated by the light source with an incident angle of 45°. The reflection light which is reflected from the sample material is received by the photo detector with a receiving angle of 0°. The reflection rate (Yb) of the reflection light is detected by the photo detector.

The opacity (OP) is obtained by the following formula:

$$OP(\%) = (Yb/Yw) \times 100 \quad (1)$$

This process is repeated for one sample sheet material at least five times and the average value of the opacities (OP) measured is calculated and recorded by the colorimeter. The average value of the opacities measured is called the opacity of a sheet material.

II. Total Color Difference ($\Delta E^*$) under CIE 1976 L*a*b*

Preferably, the same dispersion colorimeter is also used for determining the total color difference of a sample material, except that the measurements should be conducted by using a light source "D50 (i.e., an approximation of daylight having a correlated color temperature of about 5000K)," at a viewing angle of 10° (degrees).

The measurement and calculation for the total color difference ($\Delta^*E$) is defined by CIE 1976 L*a*b*: CIE Publication 15.2 (1986) by using the white standard plate which has the standard white color (L*=93.95, a*=0.26, b*=4.95).

Before the measurement, a sheet material to be measured are piled up ten sheets to form a sample material.

In the measurement, the white standard plate is placed on the flat table. The sample material (i.e., the ten piled sheets) or the pseudo-sample material is put on the white standard plate in a flat state. The sample material is illuminated by the light source with an incident angle of 45°. The reflection light which is reflected from the sample material is received by the photo detector with a receiving angle of 0°. The reflection light is detected by the photo detector. The detected reflection light is converted into the luminosity (L*1), the red-green chromaticity (a*1), and the yellow-blue chromaticity (b*1) by the colorimeter.

After the sample sheet material is replaced with the standard white surface, the above measurement is conducted for the standard white surface. The detected reflection light by the photo detector is converted into the luminosity (L*w), the red-green chromaticity (a*w), and the yellow-blue chromaticity (b*w) by the colorimeter.

The above process is repeated for each material at least five times and the average values L*1, a*1, b*1, L*w, a*w, and b*w are calculated and recorded by the colorimeter. Thus, two sets of photo data (L*1, a*1, b*1) and (L*w, a*w, b*w) are obtained. The total color difference value ($\Delta^*E$) is then obtained by the following formulas:

$$\Delta L^* = L^*1 - L^*w \quad (2)$$

$$\Delta a^* = a^*1 - a^*w \quad (3)$$

$$\Delta b^* = b^*1 - b^*w \quad (4)$$

$$\Delta E^* = \sqrt{((\Delta L^*)^2 + (\Delta a^*)^2 + (\Delta b^*)^2)} \quad (5)$$

These data are calculated and recorded by the colorimeter.

III. Hue Angle Difference ($\Delta h$)

Two sample sheet materials S1 and S2 are prepared. The above process for the total color difference is repeated for each material S1 and S2 at least five times and the average values L*1, a*1, b*1, L*2, a*2, and b*2 are calculated and recorded by the colorimeter. Thus, two sets of photo data (L*1, a*1, b*1) and (L*2, a*2, b*2) are obtained. The hue angle differences (h1 and h2) are then obtained for each material S1 and S2 by the following formulas:

$$h1 = \tan^{-1}(b^*1/a^*1) \quad (6)$$

$$h2 = \tan^{-1}(b^*2/a^*2) \quad (7)$$

The hue angle difference ($\Delta h$) is then obtained by the following formula:

$$\Delta h = h1 - h2 \quad (8)$$

(Notes for the above II and III)

If a sample sheet material has more than one color, one particular color which occupies the greatest area of the sample sheet material compared with the other color(s) is identified as a "primary color". In the measurement, such a sample sheet material is replaced with a modified sample sheet material which has only the primary color uniformly in the whole area. The modified sample sheet material is used as a sample sheet material in the measurement. For example, if a sample sheet material has a blue color area which is the greatest compared with the other color area(s), the blue color is identified as the primary color in the sample sheet material.

IV. Speculum Gloss (Gs)

A gloss meter is preferably used for determining the speculum gloss of a sample material. A preferred gloss meter is available from K. K. Horiba, Kyoto, Japan, under Trade Name "Handy Gloss Checker" (IG-330).

This gloss meter includes a light source for Illuminant A (i.e., an approximation of incandescent lamp having a correlated color temperature of about 3000 K), a flat table, a black glass plate (as the calibration standard plate), a photo detector which includes a photo-detector, and a computer. The black glass plate has a predetermined speculum gloss ($G_0$=90). under 60 degrees system.

Before starting the measurement, the gloss meter is calibrated by using the calibration standard plate. I.e., the measuring instrument which has a light source and a photo detector is put on the calibration standard plate in a flat state. The calibration standard plate is illuminated by the light source with an incident angle of 60°. The reflection light which is reflected from the sample material is received by the photo detector with a receiving angle of 60°. The intensity (φo) of the reflection light is detected by the photo detector.

In the measurement, the calibrated measuring instrument is put on the a sample material in a flat state. The sample material is illuminated by the light source with an incident angle of 60°. The reflection light which is reflected from the sample material is received by the photo detector with a receiving angle of 60°. The intensity (φs) of the reflection light is detected by the photo detector and the speculum speculum gloss (Gs) is calculated and obtained using following formula by the equipment $$Gs=(\phi s/\phi o)\times G_0 \quad (9)$$

$G_0$ is the speculum gloss of the standard plate ($G_0$=90)

This process is repeated for each material at least five times and the average value of the speculum gloss (Gs) measured is calculated and recorded by the computer. The average value of the speculum gloss measured is called the speculum gloss of a sheet material.

V. UV Transmittance (UVT)

A UV spectrophotometer is preferably used for determining the UV transmittance of a sample material. A preferred UV spectrophotometer is available from Shimadzu Corporation, Kyoto, Japan, under Code No. UV-3600.

This spectrophotometer is a double-beam style and includes a sample holder and a reference holder having open windows. The light source is placed away from one side of the sample/reference holder, while the detector is placed away from the other side of the sample holder.

The measurement has the following conditions: the wave range: 250 nm to 400 nm; the observed wave length: 340 nm; the operation mode: "transmission"; the slit width: 2.0 nm; the scan-speed: "medium"; and the beam area: W 2.0 mm×H 17.0 mm.

Before the measurement, a sheet material is cut into a rectangular piece having 3 cm×4 cm sizes. The product outer side of the sample piece is directed to the light source, and it is attached to the sample holder by scotch tape. The scotch tape is not attached on the beam application area of sample. There is no sample on the reference holder.

In the measurement, the spectrophotometer is turned on and wait for at least 30 minutes for warm-up. The light passes trough both the reference holder and the sample holder. The reference light volume (Vr) and the sample light volume (Vs) is then detected and recorded by the computer. The computer then calculates the UV transmittance (UVT) by the following formula;

$$UVT=(Vs/Vr)\times 100(\%) \quad (10)$$

The UVT value is read at the wave length of 340 nm. This process is repeated at least three times for each material and the average values of the UVT is obtained.

It is understood that the examples and embodiments described herein are for illustrative purpose only and that various modifications or changes will be suggested to one skilled in the art without departing from the scope of the present invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A packaged absorbent article, comprising:
   a. a wrapper sheet that is in the form of a pouch and that comprises a non-white coloration treatment that is not printing and that comprises a CIE L*a*b* hue angle from −40 degrees to 20 degrees; and
   b. an absorbent article disposed in the pouch, the absorbent article comprising a garment facing surface that comprises a second non-white coloration treatment also comprising a CIE L*a*b* hue angle from −40 degrees to 20 degrees;
   c. wherein the absorbent article is folded but not folded together with the wrapper sheet.

2. The packaged absorbent article of claim 1, wherein the wrapper sheet comprises a nonwoven.

3. The packaged absorbent article of claim 1, wherein the wrapper sheet has an opacity of about 8.5% to about 50%.

4. The packaged absorbent article of claim 1, wherein the wrapper sheet has a UV transmittance of about 0 to about 35.

* * * * *